(12) United States Patent
Eichenseer

(10) Patent No.: US 7,899,884 B2
(45) Date of Patent: Mar. 1, 2011

(54) METHOD AND SYSTEM FOR PROVISION OF IMAGE DATA FROM A SERVER TO A CLIENT

(75) Inventor: Mario Eichenseer, Pinzberg (DE)

(73) Assignee: Siemens Aktiengesellschaft, Munich (DE)

( * ) Notice: Subject to any disclaimer, the term of this patent is extended or adjusted under 35 U.S.C. 154(b) by 244 days.

(21) Appl. No.: 12/175,834

(22) Filed: Jul. 18, 2008

(65) Prior Publication Data

US 2009/0043841 A1 Feb. 12, 2009

(30) Foreign Application Priority Data

Jul. 20, 2007 (DE) .......................... 10 2007 033 900

(51) Int. Cl.
*G06F 15/16* (2006.01)
(52) U.S. Cl. ........................................ 709/217
(58) Field of Classification Search .................. 709/201, 709/203, 217
See application file for complete search history.

(56) References Cited

U.S. PATENT DOCUMENTS

| | | | |
|---|---|---|---|
| 6,574,629 B1 * | 6/2003 | Cooke, Jr. et al. ..................... | 1/1 |
| 2002/0099853 A1 * | 7/2002 | Tsujii et al. .................... | 709/247 |
| 2006/0168338 A1 | 7/2006 | Bruegl et al. | |
| 2006/0241979 A1 * | 10/2006 | Sato et al. .......................... | 705/3 |

* cited by examiner

*Primary Examiner* — Wing F Chan
*Assistant Examiner* — Andrew Woo
(74) *Attorney, Agent, or Firm* — Schiff Hardin LLP

(57) ABSTRACT

In a method, a device and a computer program product for provision of image data such as thin slice image data and thick slice image data of a server to a client, the image data having been acquired by an imaging modality and being cached in a cache acting as a server; the image data are provided to the client by involving the client in data exchange with the server, and an information system that is likewise involved in data exchange with the server is always automatically informed about a current state of the cache, in particular about thin slice image data available in the cache. The client directly or indirectly accesses the image data of the cache for automatic provision of the image data.

7 Claims, 1 Drawing Sheet

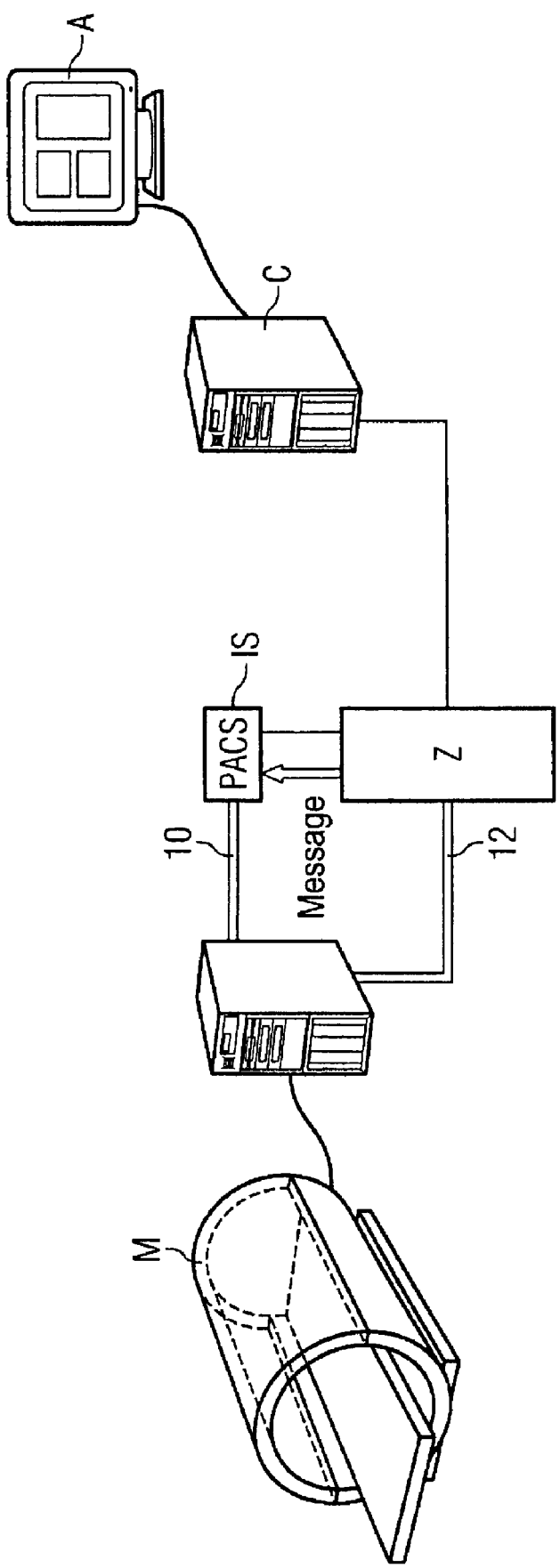

METHOD AND SYSTEM FOR PROVISION OF IMAGE DATA FROM A SERVER TO A CLIENT

BACKGROUND OF THE INVENTION

1. Field of the Invention

The present invention is in the fields of medical technology and information technology and in particular concerns the provision to a client of image data that have been acquired by means of imaging methods, in particular provision of thin slice image data and thick slice image data obtained by a radiological apparatus.

2. Description of the Prior Art

In principle, image data are acquired by means of a detector of an imaging modality (for example a computed tomography apparatus) and are subsequently relayed to a computer associated with the modality for post-processing and, when necessary, for further processing. Depending on the required resolution for the images, thin slice image data and thick slice image data are differentiated. The scan of a specific body region (for example of the thorax) with a predetermined scan range and a determined overlap factor (overlap) generates, for example, a count of 30 thick slice image data and a count of 750 thin slice image data. From this example it is clear that the volume of the thin slice image data is higher by a multiple than the volume of the corresponding thick slice image data.

For making a finding (medical assessment) with respect to a patient, it is necessary that all acquired image data be considered, and thus displayed at a client of a server that is designed for this purpose.

It is known to use a system known as a PACS (Picture Archiving and Communication System) in order to store acquired image data. In such conventional systems in use, only the thick slice data are directed via the PACS. The much more comprehensive thin slice image data are not recorded in the PACS, but instead are stored or buffered in a temporary cache. For further processing of these thin slice image data, it is a very significant disadvantage that, in conventional systems, this cache is in no way communicatively linked with an information system such as, for example, with a radiological information system (RIS) or a hospital information system (HIS).

If it becomes necessary in the context of the finding to access the data of a patient (in particular thick slice and thin slice image data), this is currently possible only by the user manually locating the storage location of such data in order to then download or to print out the image data from the user's computer. This procedure has proven to be very laborious and error-prone.

SUMMARY OF THE INVENTION

An object of the present invention is to improve the display and provision of medical image data (in particular of thin slice image data) as well as the subsequent further processing thereof. In particular, flexibility in the provision of such data should be increased and the access to such data should be automated.

The object is achieved in accordance with the invention by a method for provision of image data to a client of a server, wherein the image data have been acquired by an imaging modality and are stored or accessible in a temporary cache acting as the server, wherein the image data are provided to a client (in particular for display) that is involved in data exchange with the cache; wherein the information system (that likewise is involved in data exchange with the cache) is always automatically informed about a current state of the cache, in particular about image data available in the cache; and wherein the client and/or the information system accesses the image data of the cache to automatically provide the image data to the client.

In the preferred embodiment, the image data are thick slice image data and/or thin slice image data that have been acquired by an imaging modality. Computed tomography systems and image data generated by such systems are the primary field of application of the method according to the invention. In one embodiment, the method is designed only for thin slice image data; in another embodiment, the method is designed only for thick slice image data; and in yet another embodiment, the method concerns combinations of these two data types mentioned in the preceding, and alternative embodiment can concern yet further image data.

The client is normally a computer-supported workstation that can be fashioned as a stand-alone PC, as a more complex workstation, or as a cluster of computers. Moreover, it is possible to fashion the client as a mobile, wearable device, for instance in the form of a PDA, handheld communication devices, Bluetooth devices, etc. The clients are designed to execute additional processing steps on the acquired image data, for example in the context of a finding and/or diagnosis. The client is typically involved in a communication connection or in data exchange with the temporary cache in which the thin slice image data are stored and which acts as a server in order to be able to provide the thick slice image data of the information system. The client can access the cache directly or indirectly (thus via additional computer modules). The client indirectly accesses the thick slice image data via the cache acting as a server, which thick slice image data are stored in the information system (for example PACS).

The information system can be a clinic-internal or clinic-extensive computer-supported information system, for example a hospital information system (HIS) or (in the case of radiology departments) a radiology information system (RIS). Moreover, it is possible to fashion the information system as a PACS, or as a combination of the systems mentioned in the preceding, or with additional modules and/or interfaces.

As used herein, the term "provision of data" is broadly understood and, in addition to an access procedure, also concerns the display of the requested data on a monitor of the client. Moreover, additional processing steps can be encompassed with this term such as, for example, loading of the data, and formatting and/or conversion of the data. For purposes of security it is likewise possible that the provision likewise includes an encryption and decryption of the data. Image data requested by a client can be automatically presented on the monitor of the client. Alternatively, a notification can be made to appear on the screen of the client before the provision of the data to the client, this notification providing a message about the predicted load time of the data. This is particularly useful when the required image data are no longer located in a temporary cache but rather have already been released to further storage entities, such that a downloading of the required image data is associated with longer wait times. It is likewise possible to specify the exact storage location of the required data in the event that the required data are no longer located in the cache.

In principle, the method according to the invention is to provide a physician with all relevant image data that have been acquired at one or more different modalities within the framework of making a finding. This should be enabled without the physician having to manually search for the data; rather, an automatic loading and display of the image data should be ensured. Particular attention is for all thin slice image data to be automatically provided in addition to the thick slice image data. Alternative embodiments, however, provide that further image data and/or further findings are automatically displayed and/or provided to the physician in addition to the radiological images.

In a preferred embodiment, the method according to the invention accesses a PACS that can be designed to provide the thick slice image data. Depending on the usage or application purpose, the PACS can naturally also encompass further functionalities and be used for other services.

The cache can be fashioned as an individual, computer-based module integrated into the network or as an add-on module that is connected as an accessory to already-present modules. It is involved in data exchange with the information system, the client and (directly or indirectly) the imaging modality.

A proprietary interface is provided between client and server. Furthermore, a data interface between the server and the information service RIS or HIS is provided. In an alternative embodiment, a communication module can be provided as a separate instance that is connected to the PACS, RIS and/or HIS (as known in the prior art) and that functions as a communication instance with the respective temporary cache acting as a server. The system according to the invention thus can be designed more modularly and is thereby more flexible in its usage, allowing existing systems to also be used.

A further aspect of the present invention is that at least the information system is automatically informed about the current state of the cache. The state information can include a statement as to which thin slice image data are presently located in the temporary cache. The specific storage location at which the respective thin slice data are currently stored thus can be unambiguously tracked within the system. In particular, the cache can automatically send an input notification (MESSAGE-IN) to the information system as soon as image data are loaded into the cache. After the acquisition by means of a detector, the data are typically processed further by means of a computer associated with the detector and are thereupon loaded into the cache for storage. As soon as this occurs, the input notification is emitted as an output. Moreover, an output notification (MESSAGE-OUT) can be sent to the information system when image data from the cache are altered, deleted and/or relayed to other modules or instances or are subjected to other modifications. Thus, the data content at client is narrated at the server.

In a more complex embodiment of the present invention, the messages are designed more broadly or comprehensively and include a count, a slice thickness of the images and/or information about the imaging method for the acquired images in addition to the patient data (such as, for example, the name, the access number, the requested procedure ID, the study ID). If a patient is identified by his or her individual identifier via the patient's data set (for example by double-clicking on the respective data set) in the framework of making a finding for that patient, the information contained in the messages also automatically appear in addition to an electronic work list for the radiologist and in addition to the thick slice data and/or thin slice data or image data which can be automatically accessed. In other words, given a selection of a respective patient in the patient list (for example via a double-click), as already mentioned not only are the patient's thick slice images automatically displayed from the PACS, but also the patient's thin slice images on an additional client opened at a further monitor or the same monitor.

In a preferred embodiment, the message has or the messages have a standardized form, for example as a DICOM message, and can (for example) be sent to the RIS system in the form of what are known as a "Storage commitments".

In a further preferred embodiment, the provision of the image data to the client or on a monitor of the client includes an automatic presentation or display of all image data in the event that the respective patient has been selected or identified by the user, which triggers an automatic request of that patient's image data. A client can also automatically pop up on a monitor, this pop-up client being designed to provide the thin slice and thick slice image data or, respectively, directs the user in this regard. It is therefore ensured that the assessing physician considers all relevant image data and obtains an overview of the available image material. The quality of the diagnosis as a whole thus can be distinctly increased by all high-quality CT thin slice images or additional user interactions and control commands being displayed.

In a preferred embodiment the cache for storage of the thin slice image data is designed as a server that can operate a number of clients. It is possible for the cache acting as a server to directly display the requested thin slice image data on the respective client (while they remain on the server), or it can do this via a communicator entity (for example a separate communication module). The respective entities or modules in use are connected with one another via a network and thus are engaged in data exchange. A fast loading of thin slice images thus can be achieved.

In a further preferred embodiment, given a request for image data that are no longer located in the temporary cache, an automatic search within the system is automatically triggered in order to locate the current storage location for the requested image data. This makes it possible for the requested image data to be automatically provided to the client without the user having to output a separate user interaction or a corresponding command.

As mentioned in the preceding, the solution according to the invention can also be fashioned as a computer program product or as a product formed by hardware and/or software modules. The claimed device includes a cache acting as a server, the cache is designed for buffer storage of the thin slice image data, an information system that is engaged in data exchange with the cache and that is always automatically informed about a current state of the cache, and a client to which the image data should be provided and that therefore accesses the image data of the cache.

In a preferred embodiment, the device or product described in the preceding includes a notification module that is designed to output and/or to receive notifications or messages about the current (load) state of the cache, and in particular sends an input notification as soon as data are loaded into the cache and sends an output notification (in particular to the information system) in the event that image data in the cache are modified in any way, erased or have been relayed to other entities.

BRIEF DESCRIPTION OF THE DRAWINGS

The single FIGURE is an overview representation of the design and the mode of operation for image data provision according to the invention.

DESCRIPTION OF THE PREFERRED EMBODIMENTS

The method according to the invention provides image data 10, 12 that have been acquired by an imaging modality (for example by a computed tomography apparatus M). Thick slice image data 10 and thin slice image data 12 thereby accumulate.

As shown in the FIGURE, the image data 10, 12 acquired by a detector are relayed from the CT scanner of the modality M to a computer associated with it; for further processing or caching the thick slice data 10 are typically relayed to a PACS system that acts as an information system IS. According to the invention, the thin slice image data 12 are relayed to a temporary cache Z for buffer storage, which cache Z acts as a server. The cache is involved in data exchange with the information system IS. In an achievement of the invention, a long-term archive is additionally provided in which the data streams of thin slice image data 12 and thick slice image data 10 are recombined and stored for long term storage. Corresponding interfaces to the PACS and memory Z are provided. The information system IS can be a PACS, a radiology information system (RIS) and/or a hospital information system (HIS). So that only an assessing physician or other user can access the data 10, 12 acquired by the modality M, a client C is provided to which at least one display device A or monitor is connected that is designed to display and present all image data representing thick slice image data 10 and thin slice image data 12.

The modality M thus serves as a data generator of thin and thick slice image data 10, 12. The data stream of thin and thick slice image data 10, 12 is then branched into two data streams: into a thin slice data stream 12 to an application server and temporary cache Z and into a thick slice data stream 10 to the PACS server. Both data streams can be recombined, for example in a long term archive (not shown in FIG. 1). Both the PACS server and the application server have clients that can (but do not necessarily have to) physically run on a computer. An RIS and an HIS server with clients exist in parallel to the PACS server and application server. These can also physically run on a computer. It is likewise possible that all (four) of the clients mentioned in the preceding run on one computer.

Normally, different clients C are connected both to the PACS that acts as an information system IS and to the temporary cache Z. In other words, different clients C are provided: one for the temporary cache Z and one for the RIS server or, respectively, one for the KIS server or, respectively, one for the PACS server. In alternative embodiments it can thus be provided that further modules or, respectively, instances of the information system IS are provided or, respectively, act as information systems in addition to the PACS. It is also possible that exclusively the PACS is used by the memory Z acting as the server or communicator.

An input notification is output as soon as thin slice image data 12 are imported or, respectively, loaded into the cache Z. This advantageously ensues from the cache Z itself. The notification is advantageously sent to the information system IS in order to inform said information system IS that new data sets 12 have been load into the cache Z. Alternatively, it is also possible to send the input notification to a different entity.

Moreover, a notification of change is always output in the event that a change to the load state of the cache Z or, respectively, to the data loaded in it results. This is the case, for example, when thin slice image data 12 already loaded into the cache Z are modified in any way, related to other modules or deleted. In this case the notification of change is advantageously sent to the information system IS. As mentioned above, the notification of change can be supplied as an output directly to a different entity. This means this information is also sent to the information system IS as a notification of change in the form of a DICOM message in the event that images are erased or have been sent on from the server acting as a cache Z. Insofar as the images have only been sent to another server (within the network), an automatic search and automatic access to the respective patient images from the server on which the current image data 10, 12 are located is executed upon double clicking on a corresponding symbol on a patient from the patient list on the user interface of the client C. Otherwise, in the event that the images have already been moved to a further instance that is not accessible within the network, it can be provided that a corresponding message is output that informs where the image data 10, 12 are presently stored and which parties must be informed for an access to the image data.

In further embodiments of the invention, additional notifications are provided that are output either by the cache Z or the PACS system. The notification can be configured differently depending on the application case. In addition to the patient data (for example, in addition to the name, the access number, the required procedure ID, the study ID etc.), this notification typically also includes the count and the slice thickness of the images as well as the underlying imaging method. Moreover, it is possible to include additional information therein.

As shown in the FIGURE, the PACS system as an information system IS and the cache Z acting as a server are engaged in a communication connection. A communication connection between client C and the information system IS is not provided in the preferred embodiment. The data exchange between information system IS and client C is communicated via the cache acting as a server.

It will be apparent to those skilled in the art that the invention can be realized partially or entirely in software and/or hardware and/or distributed among multiple physical products (in particular, computer program products).

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for providing image data to a client, comprising the steps of:

in a processor, dividing image data acquired by an imaging modality into a thin slice image data stream, consisting of thin slice image data acquired by said imaging modality, and a thick slice image data stream, consisting of thick slice image data acquired by said imaging modality;

directing said thin slice image data stream to a cache server and storing said thin slice image data in said cache server;

directing said thick slice image data stream to a memory of an information system, separate from said cache server, and storing said thick slice image data in said memory;

establishing a data change relationship between said cache server and a client of said cache server allowing said client to access said thin slice image data stored in said cache server, and automatically providing said thin slice image data from said cache server to said client via said data exchange relationship upon said client accessing said thin slice image data stored in said cache server;

establishing a further data exchange relationship between said cache server and said information system, and allowing said client of said cache server to access said thick slice image data from said memory of said information system via said data exchange relationship between said cache server and said client and said further data exchange relationship between said cache server and said information system; and always automatically informing said information system, via said further data exchange relationship between said cache server and said information system, as to a current content state of said thin slice image data stored in said cache server.

2. The method as claimed in claim 1 comprising automatically informing said information system about a current image data content state of the cache functioning as a server by emitting an input notification to the information system from the cache functioning as a server, via the data exchange relationship between the cache functioning as a server and the information system, as soon as said image data are loaded into the cache functioning as a server, and by sending a change notification from the cache functioning as a server to the information system, via the data exchange relationship between the cache functioning as a server and the information system, as soon as said image data are altered or deleted or relayed to another storage entity.

3. The method as claimed in claim 1 comprising automatically displaying, at a monitor of the client, all image data that are accessed from the cache functioning as a server by the client.

4. A system for providing image data to a client, comprising:
- a processor;
- an information system comprising a memory;
- a cache server;
- said processor being configured to divide image data acquired by an imaging modality into a thin slice image data stream, consisting of thin slice image data acquired by said imaging modality, and a thick slice image data stream, consisting of thick slice image data acquired by said imaging modality and to direct said thin slice image data stream to said cache server and said cache server storing said thin slice image data therein and to direct said thick slice image data stream to said memory of said information system, said memory storing said thick slice image data therein;
- said cache server being configured to establish a data change relationship between said cache server and a client of said cache server that allows said client to access said thin slice image data stored in said cache server, and to automatically provide said thin slice image data from said cache server to said client via said data exchange relationship upon said client accessing said thin slice image data stored in said cache server;
- said cache server being configured to establish a further data exchange relationship between said cache server and said information system, that allows said client of said cache server to access said thick slice image data from said memory of said information system via said data exchange relationship between said cache server and said client and said further data exchange relationship between said cache server and said information system; and
- said cache server being configured to always automatically inform said information system, via said further data exchange relationship between said cache server and said information system, as to a current content state of said thin slice image data stored in said cache server.

5. The system as claimed in claim 4 wherein said cache functioning as a server is configured to automatically inform said information system about a current image data content state of the cache functioning as a server by emitting an input notification to the information system from the cache functioning as a server, via the data exchange relationship between the cache functioning as a server and the information system, as soon as said image data are loaded into the cache functioning as a server, and by sending a change notification from the cache functioning as a server to the information system, via the data exchange relationship between the cache functioning as a server and the information system, as soon as said image data are altered or deleted or relayed to another storage entity.

6. The system as claimed in claim 4 comprising a monitor at the client at which all image data that are accessed from the cache functioning as a server by the client are automatically displayed.

7. A non-transitory storage medium encoded with programming instructions, said storage medium being accessibly by respective processors in a computerized system comprising an information system having a memory, and a cache server separate from said information system said programming instructions causing said processors to:
- divide image data acquired by an imaging modality into a thin slice image data stream, consisting of thin slice image data acquired by said imaging modality, and a thick slice image data stream, consisting of thick slice image data acquired by said imaging modality;
- direct said thin slice image data stream to a cache server and storing said thin slice image data in said cache server;
- direct said thick slice image data stream to a memory of an information system, separate from said cache server, and storing said thick slice image data in said memory;
- establish a data change relationship between said cache server and a client of said cache server allowing said client to access said thin slice image data stored in said cache server, and automatically providing said thin slice image data from said cache server to said client via said data exchange relationship upon said client accessing said thin slice image data stored in said cache server;
- establish a further data exchange relationship between said cache server and said information system, and allowing said client of said cache server to access said thick slice image data from said memory of said information system via said data exchange relationship between said cache server and said client and said further data exchange relationship between said cache server and said information system; and
- always automatically inform said information system, via said further data exchange relationship between said cache server and said information system, as to a current content state of said thin slice image data stored in said cache server.

* * * * *